US008992536B2

(12) United States Patent
Piza Vallespir et al.

(10) Patent No.: US 8,992,536 B2
(45) Date of Patent: Mar. 31, 2015

(54) COPLANAR DEFORMITY CORRECTION SYSTEM

(75) Inventors: Gabriel Piza Vallespir, Santa Eugenia (ES); Qui Yong, Nanjing (CN); Mingyan Liu, Bourg la Reine (FR); Jeffrey Zhang, Collierville, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 246 days.

(21) Appl. No.: 13/168,797

(22) Filed: Jun. 24, 2011

(65) Prior Publication Data

US 2011/0319938 A1 Dec. 29, 2011

(30) Foreign Application Priority Data

Jun. 24, 2010 (CH) .............................. 201010218781

(51) Int. Cl.
*A61B 17/70* (2006.01)
(52) U.S. Cl.
CPC ......... *A61B 17/7085* (2013.01); *A61B 17/7076* (2013.01); *A61B 17/708* (2013.01)
USPC ........................................ 606/86 A; 606/279
(58) Field of Classification Search
USPC ................... 606/86 A, 86 R, 87, 90, 246–279
See application file for complete search history.

(56) References Cited

U.S. PATENT DOCUMENTS

| 2,687,720 A | 8/1954 | Haboush |
| 3,865,105 A | 2/1975 | Lode |
| 4,078,559 A | 3/1978 | Nissinen |
| 4,112,935 A | 9/1978 | Latypov et al. |
| 4,274,401 A | 6/1981 | Miskew |
| 4,361,141 A | 11/1982 | Tanner |
| 4,361,144 A | 11/1982 | Slatis et al. |
| 4,409,968 A | 10/1983 | Drummond |
| 4,505,268 A | 3/1985 | Sgandurra |
| 4,641,636 A | 2/1987 | Cotel |
| 4,854,304 A | 8/1989 | Zieike |
| 5,102,412 A | 4/1992 | Rogozinski |
| 5,219,349 A | 6/1993 | Krag et al. |
| 5,261,908 A | 11/1993 | Campbell, Jr. |
| 5,281,223 A | 1/1994 | Ray |
| 5,391,168 A | 2/1995 | Sanders |

(Continued)

FOREIGN PATENT DOCUMENTS

| DE | 8912943 U1 | 11/1987 |
| DE | 3807335 A1 | 9/1989 |

(Continued)

*Primary Examiner* — Eduardo C. Robert
*Assistant Examiner* — Steven Cotroneo

(57) ABSTRACT

A bone anchor assembly is provided, which may be used in cervical, thoracic, lumbar or sacral areas of the spine or other orthopedic locations. The anchor assembly includes a bone anchor, a receiver mounted to the bone anchor, a saddle within the receiver, a spacer within the receiver, and an engaging member. The receiver extends along a central longitudinal axis proximally away from the bone anchor. A rod or other elongated connecting element is received in a passage of the receiver in contact with the saddle, and the engaging member engages the connecting element against the saddle, which engages the saddle against the spacer, which in turn engages the proximal head of the bone anchor in the receiver. The orientation of the saddle in the receiver is adjustable to correspond to the orientation of the connecting element relative to the central longitudinal axis of the receiver.

10 Claims, 12 Drawing Sheets

(56) References Cited

U.S. PATENT DOCUMENTS

| | | |
|---|---|---|
| 5,425,732 A | 6/1995 | Ulich |
| 5,478,340 A | 12/1995 | Kluger |
| 5,531,747 A | 7/1996 | Ray |
| 5,582,612 A | 12/1996 | Lin |
| 5,591,165 A | 1/1997 | Jackson |
| 5,591,167 A | 1/1997 | Laurain et al. |
| 5,603,714 A | 2/1997 | Kaneda et al. |
| 5,607,425 A | 3/1997 | Rogizinski |
| 5,662,652 A | 9/1997 | Schafer et al. |
| 5,702,392 A | 12/1997 | Wu et al. |
| 5,720,751 A | 2/1998 | Jackson |
| 5,797,910 A | 8/1998 | Martin |
| 5,944,720 A | 8/1999 | Lipton |
| 5,951,555 A | 9/1999 | Rehak et al. |
| 6,214,004 B1 | 4/2001 | Coker |
| 6,235,028 B1 | 5/2001 | Brumfield et al. |
| 6,302,888 B1 * | 10/2001 | Mellinger et al. ............ 606/270 |
| 6,458,132 B2 * | 10/2002 | Choi ............................ 606/267 |
| 6,530,929 B1 | 3/2003 | Justis et al. |
| 6,551,320 B2 | 4/2003 | Lieberman |
| 6,565,568 B1 | 5/2003 | Rogozinski |
| 6,648,888 B1 | 11/2003 | Shluzas |
| 6,770,075 B2 | 8/2004 | Howland |
| 6,790,209 B2 | 9/2004 | Beale et al. |
| 6,805,716 B2 | 10/2004 | Ralph et al. |
| 6,694,665 B1 | 1/2005 | Thomas et al. |
| 7,250,052 B2 * | 7/2007 | Landry et al. ............... 606/86 A |
| 7,666,189 B2 * | 2/2010 | Gerber et al. ................ 606/104 |
| 8,075,592 B2 * | 12/2011 | Landry et al. ................ 606/246 |
| 8,147,524 B2 | 4/2012 | Vallespir |
| 8,162,952 B2 * | 4/2012 | Cohen et al. .................. 606/104 |
| 8,221,426 B2 * | 7/2012 | Justis et al. ................. 606/86 A |
| 2002/0138077 A1 | 9/2002 | Ferree |
| 2002/0151895 A1 | 10/2002 | Soboleski et al. |
| 2002/0173791 A1 | 11/2002 | Howland |
| 2003/0088251 A1 | 5/2003 | Braun et al. |
| 2004/0133207 A1 | 7/2004 | Abdou |
| 2004/0172022 A1 * | 9/2004 | Landry et al. .................. 606/61 |
| 2005/0033291 A1 | 2/2005 | Ebara |
| 2005/0033434 A1 | 2/2005 | Berry |
| 2005/0209694 A1 | 9/2005 | Loeb |
| 2005/0215999 A1 | 9/2005 | Birkmeyer et al. |
| 2005/0234449 A1 | 10/2005 | Aferzon |
| 2005/0245928 A1 | 11/2005 | Colleran et al. |
| 2005/0288669 A1 | 12/2005 | Abdou |
| 2006/0111712 A1 | 5/2006 | Jackson |
| 2006/0111713 A1 * | 5/2006 | Jackson ......................... 606/61 |
| 2006/0149236 A1 | 7/2006 | Barry |
| 2006/0247630 A1 * | 11/2006 | Iott et al. ........................ 606/61 |
| 2006/0264934 A1 * | 11/2006 | Fallin ............................. 606/61 |
| 2007/0213716 A1 * | 9/2007 | Lenke et al. .................... 606/61 |
| 2008/0077138 A1 * | 3/2008 | Cohen et al. .................... 606/61 |

FOREIGN PATENT DOCUMENTS

| | | |
|---|---|---|
| ES | 2201340 T3 | 3/2004 |
| FR | 2722393 A1 | 1/1996 |
| JP | 10014934 A | 1/1998 |
| WO | WO 9829046 A1 | 7/1998 |
| WO | WO 9844858 A1 | 10/1998 |

* cited by examiner

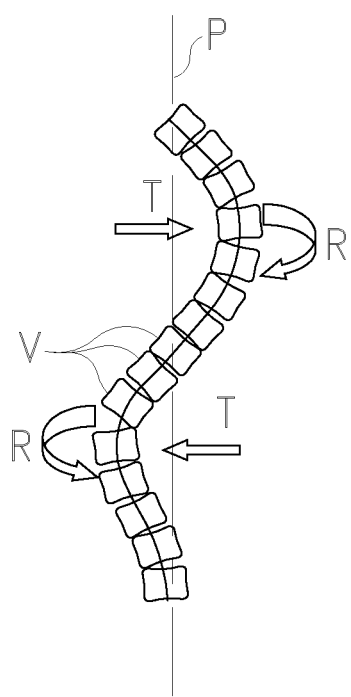 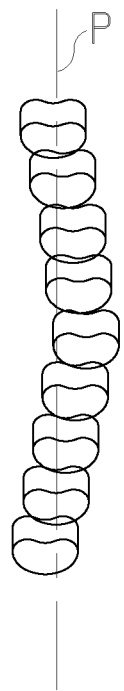
*Fig. 1*  *Fig. 2*

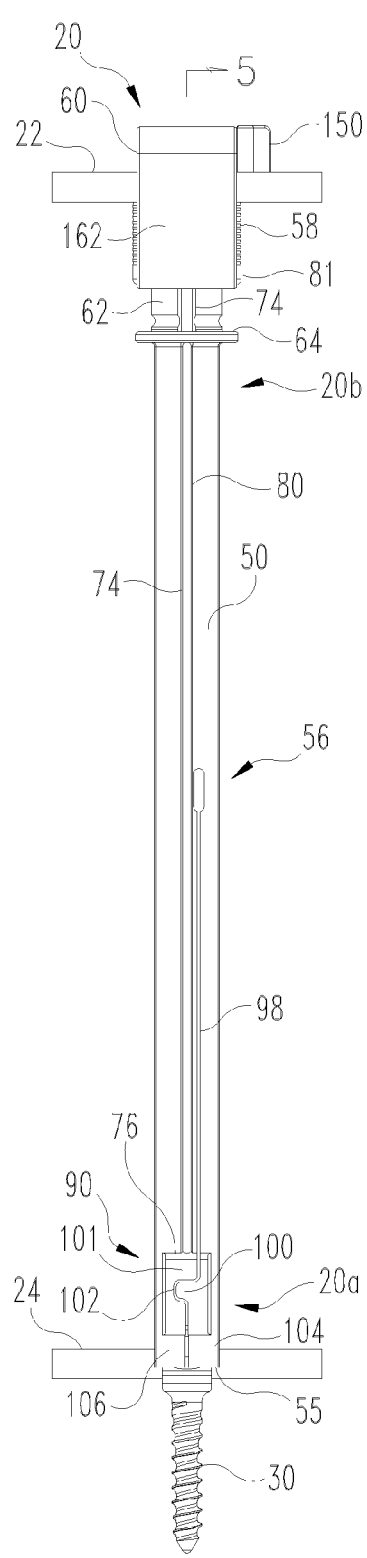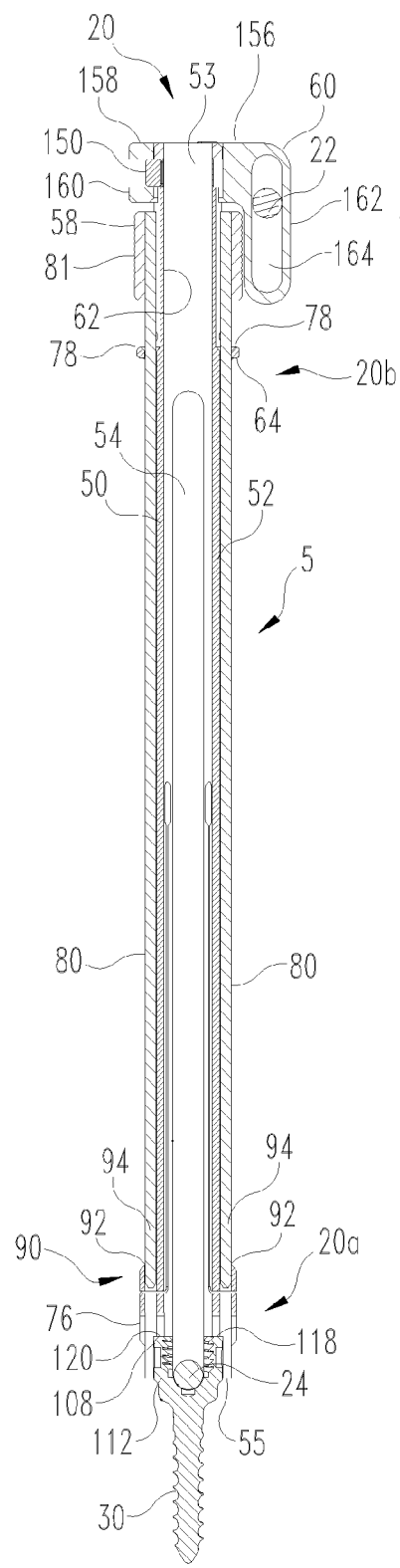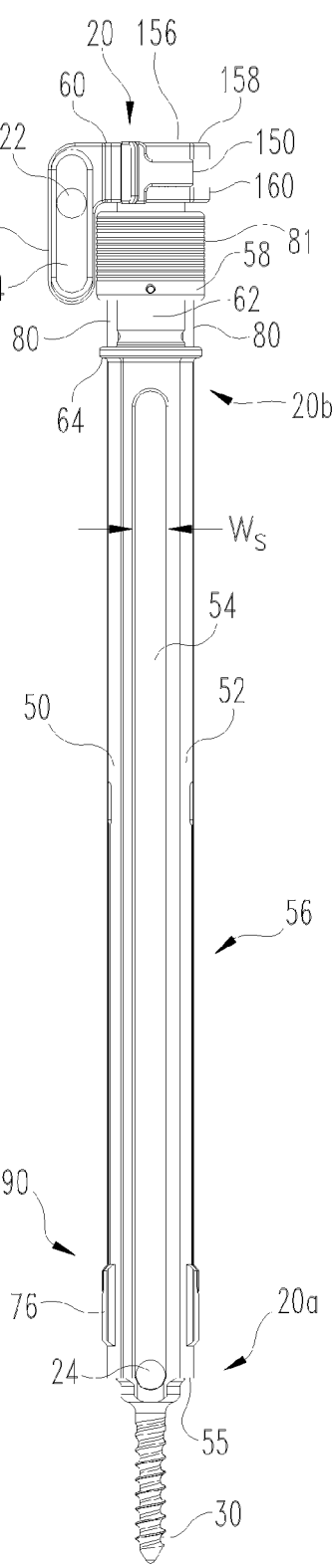
*Fig. 4*  *Fig. 5*  *Fig. 6*

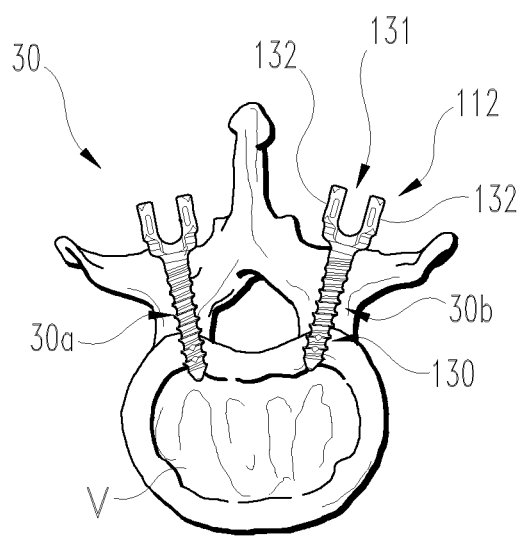
Fig. 20
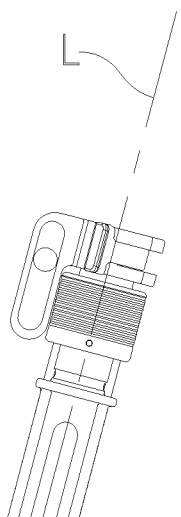
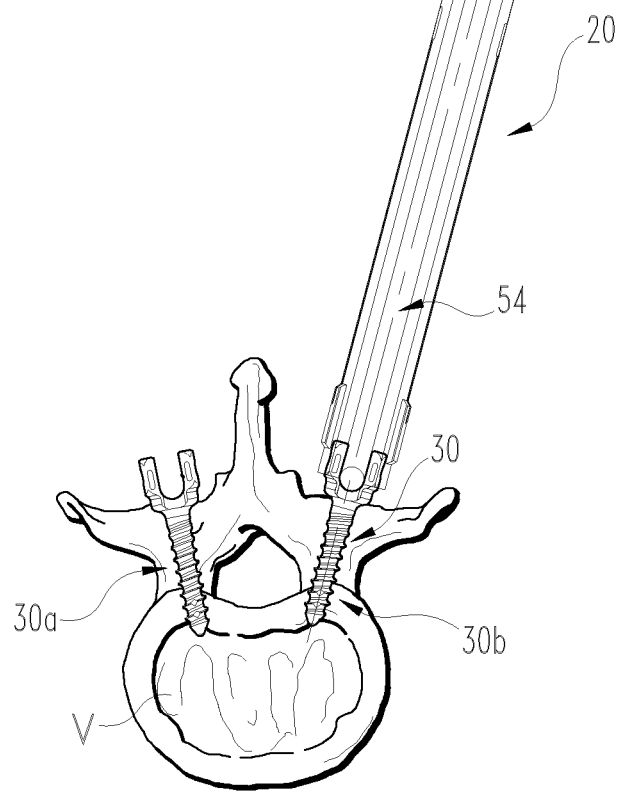
Fig. 21

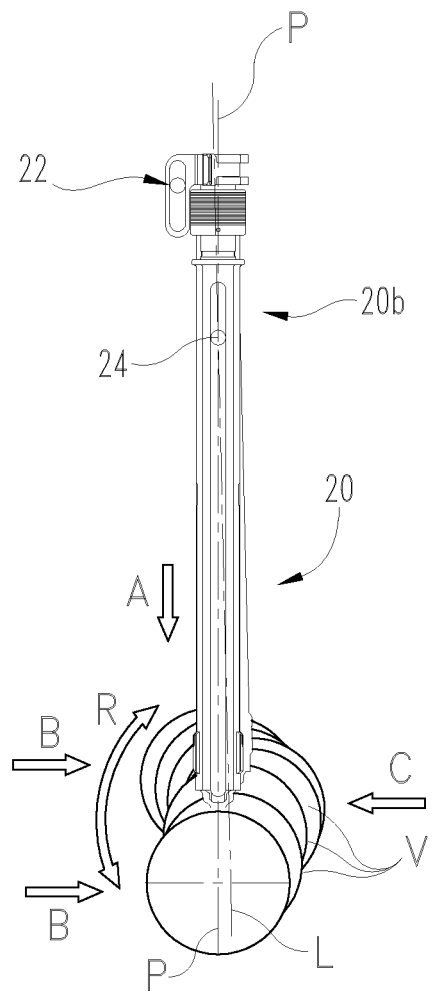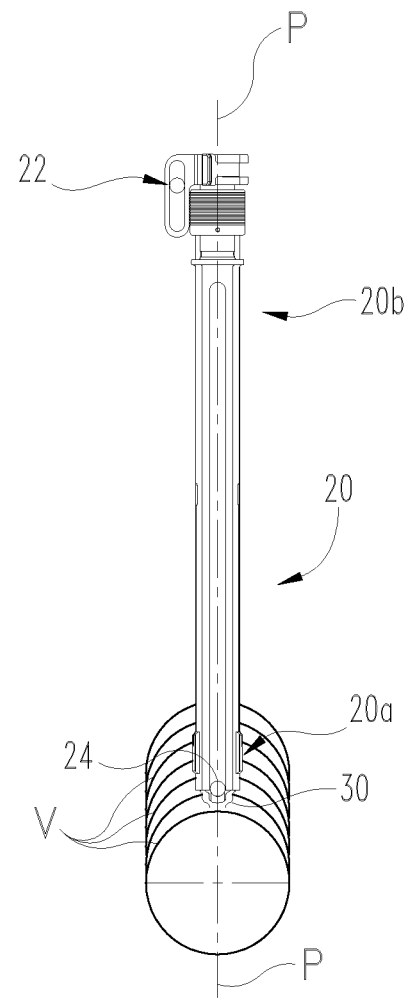
*Fig. 26*   *Fig. 27*

COPLANAR DEFORMITY CORRECTION SYSTEM

CROSS REFERENCES TO OTHER APPLICATIONS

The present application claims priority under 35 U.S.C. 119, to Chinese Patent Application Serial No. 201010218781.3, titled "Coplanar Deformity Correction System," filed Jun. 24, 2010, which is hereby incorporated herein by reference.

BACKGROUND

The present invention relates generally to treatment of the spinal column, and more particularly relates to instrumentation and methods for reducing spinal deformities including, without limitation, scoliosis.

The normal anatomy of the spinal column presents different alignment and rotational characteristics along three spatial planes. In the coronal (or frontal) plane, the vertebrae are normally aligned and present no rotation. In the transverse (or axial) plane, the vertebrae are likewise normally aligned and present neutral rotation. In the sagittal plane, the vertebrae present a certain degree of rotation and translation which form the physiological curvature of the spine; namely, cervical lordosis, dorsa or thoracic kyphosis, and lumbar lordosis.

Spinal deformities of varying etiologies are well known. Such deformities include abnormal spinal curvatures, such as, for example, scoliosis, kyphosis, and/or other abnormal curvatures wherein natural alignment of the spine is altered. With specific regard to scoliotic deformities, the abnormal curvature of the spinal column is three-dimensional. Specifically, scoliotic deformities can be separated into abnormal translation and/or rotation of the vertebrae in each of the coronal, transverse and sagittal planes. Therefore, treatment of scoliosis should preferably be aimed at addressing reduction of the abnormal curvature in each of the three spatial planes.

A number of methods and techniques have been used to reduce abnormal spinal curvatures. Most of these techniques have been based on anchoring devices onto posterior elements of the spine (e.g., via clips or wires). Such techniques reduce the translational aspects of the deformity, but have little or no effect on the rotational aspects.

Additionally, pedicle screws have been used in the treatment of scoliosis, thereby raising the possibility of derotation of the spinal column. However, techniques for treatment of scoliosis using pedicle screws are based essentially on translation to align the spinal column, either by bending or rotating a spinal rod after the rod is engaged to the screws, or by forcing the pedicle screws into engagement with the rod. Other reduction techniques provide for derotation via the use the pedicle screws, but such derotation is usually implemented following placement of the spinal rod individually and consecutively into engagement with the pedicle screws. Additionally, when pedicle screws are anchored to a scoliotic spine, the screws follow the curvature of the spine and tend to be inclined in the transverse plane depending on vertebral rotation, thereby complicating placement of the spinal rods.

Treatment of a spinal deformity via a reduction technique to address both the alignment and rotational aspects of the deformity along all three spatial planes would be desirable. Thus, there remains a need for improved instrumentation and methods for reducing spinal deformities. The present invention satisfies this need and provides other benefits and advantages in a novel and unobvious manner.

SUMMARY

According to one aspect an alignment apparatus is disclosed for use in correction of a spinal deformity. The apparatus includes an elongate alignment element extending along a first longitudinal axis and including a proximal portion and a distal portion. The elongate alignment element includes a slot extending along the longitudinal axis and defining a pair of opposing side walls running from an upper portion of the elongate alignment element on the distal portion to an end of the elongate alignment element on the proximal portion. A bone anchor receptacle is defined in the end of the elongate alignment element that is operable to receive at least a portion of a bone anchor. A locking pin assembly is slidably positioned over a first portion of the upper portion of the elongate alignment element, wherein the locking pin assembly is configured to place the bone anchor receptacle in either a locked or unlocked state. In the locked state the bone anchor is fixedly secured in the bone anchor receptacle and in the unlocked state the bone anchor receptacle is capable of being disconnected from the bone anchor. A locking cap is slidably positioned over a second portion of the upper portion of the elongate alignment element.

In one form, at least one side wall of the pair of opposing side walls includes a cutout running from the end of the proximal portion a predetermined distance up the side wall thereby creating two opposing flexible members in the at least one opposing side wall. At least a portion of the cutout defines a male member that is positioned in a female member in the at least one side wall. The locking pin assembly includes at least one locking pin extending down the longitudinal axis of the elongate alignment element and configured to fit within a passage defined in the male member and the female member thereby placing the bone anchor in the locked state. Other male and female members may also be defined by the cutout thereby providing additional locking members for the locking pin to be inserted into thereby locking the two opposing flexible members together.

In another form, the bone anchor receptacle includes at least one protrusion sized and configured to fit within a recess of the bone anchor. The locking cap can include a retaining member having a passage oriented along a second longitudinal axis substantially parallel with the first longitudinal axis. The locking cap can also include a lever configured to controllably release the locking cap from the second portion of the upper portion of the elongate alignment element.

According to another aspect an alignment apparatus for use in correction of a deformity is disclosed that includes an elongate alignment element extending along a first longitudinal axis and including a proximal portion and a distal portion. The elongate alignment element includes a first slot extending along the longitudinal axis and defining a first pair of opposing side walls running from an upper portion of the elongate element on the distal portion to an end of the elongate alignment element on the proximal portion. A bone anchor having a second pair of opposing side walls is aligned with and connected to the first pair of the opposing side walls at the end of the elongate member, wherein the first slot is aligned with a receiver of the bone anchor. The apparatus also includes a cap having a collet sized and configured to fit over an upper portion of the elongate member. The cap further includes a retaining member positioned along a side of the collet having an opening for receiving a rod.

In one form, the apparatus can include a first break point where the pair of opposing side walls of the bone anchor are aligned with and connected to the first pair of opposing side walls of the elongate alignment element. As set forth in greater detail below, the first break point is operable to allow the first pair of opposing side walls of the elongate alignment element to break away from the bone anchor. In one form, the first break point comprises a groove running around an outside perimeter of the elongate alignment element. A second slot extending downwardly from an upper surface of the elongate alignment member defines a second pair of opposing side walls on the elongate alignment element. A second break point is positioned along the second slot and is operable to allow at least a portion of the second pair of opposing side walls of the elongate alignment element to break away from the elongate alignment element.

The collet can include an alignment tab protruding inwardly from the collet. The alignment tab is sized and configured to be positioned in a second slot on the upper portion thereby inhibiting rotational movement of the cap about the first longitudinal axis. Further, the alignment tab is positioned on the collet such that the opening of the retaining member lies on a second longitudinal axis substantially parallel to the first longitudinal axis when the cap is positioned in the second slot. The opening of the retaining member on the cap and the first slot of the elongate alignment element are oriented in the same direction. The collet can also include at least one protrusion sized and configured to fit in a groove on the upper portion thereby securing the cap to the elongate alignment member.

Another aspect discloses a method of reducing a spinal deformity, comprising: providing a plurality of elongate alignment elements, a first rod, and a reduction rod, wherein each of the elongate elements extends along a longitudinal axis and includes a proximal portion, a distal portion, a locking assembly member, and a locking cap; connecting a bone anchor receptacle located in the proximal portion of the plurality of elongate alignment elements to a respective bone anchor that has been secured in a respective vertebra; locking each the bone anchor receptacle to the bone anchors with the locking assembly member; inserting the first rod through each the locking cap to maintain the distal portions in general alignment; inserting the reduction rod through a slot in each elongate alignment element; and displacing the reduction rod down the slots in a proximal direction to generally align the proximal portions of the elongate alignment elements relative to the reduction rod to reduce the spinal deformity, wherein the reduction rod is displaced down the slots until the reduction rod is positioned in a receiver located in the bone anchors.

Yet a further aspect discloses a method of reducing a spinal deformity, comprising: providing a plurality of elongate alignment elements, a first rod, and a reduction rod, wherein each of the elongate alignment elements extends along a longitudinal axis and includes a proximal portion and a distal portion, wherein each of the elongate alignment elements includes a bone anchor integrally formed on the proximal portion and a cap removably connected with the distal portion; inserting a first rod through an opening in each the cap to maintain the distal portions in general alignment; inserting the reduction rod through a slot in each elongate alignment element; and displacing the reduction rod down the slots in a proximal direction to generally align the proximal portions of the elongate alignment elements relative to the reduction rod to reduce the spinal deformity, wherein the reduction rod is displaced down the slots until the reduction rod is positioned in a receiver located in the bone anchors.

In one form, the method further comprises breaking a first opposing set of side walls off of the elongate alignment member; removing the cap from the elongate alignment member; and breaking a second opposing set of side walls off of the bone anchor thereby disconnecting the elongate alignment member from the bone anchor.

Related features, aspects, embodiments, objects and advantages of the present invention will be apparent from the following description.

BRIEF DESCRIPTION OF THE DRAWINGS

FIG. 1 is a schematical illustration of a scoliotic spine wherein the natural position and alignment of the vertebrae are altered due to abnormal vertebral translation and rotation.

FIG. 2 is a schematical illustration of a scoliotic spine wherein the anteroposterior axes of the vertebrae are shown in a non-coplanar arrangement.

FIG. 4 is a side view of an elongate alignment element according to one form of the present invention.

FIG. 5 is a cross-sectional view of the elongate alignment element shown in FIG. 4, as viewed along line 5-5 of FIG. 4.

FIG. 6 is another side view of the elongate alignment element illustrated in FIG. 4 rotated about a longitudinal axis of the elongate alignment element.

FIG. 19 is a perspective view of an upper portion of the elongate alignment element shown in FIG. 14.

FIG. 20 is a schematical illustration of a vertebra with a pair of bone anchors bilaterally anchored to the vertebra.

FIG. 21 is a schematical illustration of the bone anchors shown in FIG. 20, with the alignment element shown in FIG. 4 engaged directly to one of the bone anchors.

FIG. 26 is a schematical illustration of the alignment elements shown in FIG. 25, showing further sliding engagement of the reduction rod along the alignment elements in a proximal direction to further translate and derotate one or more of the vertebrae toward a corrected state.

FIG. 27 is a schematical illustration of the alignment elements shown in FIG. 26, showing positioning of the reduction rod in the receiver of the bone anchor thereby aligning the proximal portions generally along the transverse axis of the reduction rod and resulting in translation and derotation of the vertebrae to the corrected state.

DESCRIPTION OF THE ILLUSTRATED EMBODIMENTS

Figure 3:
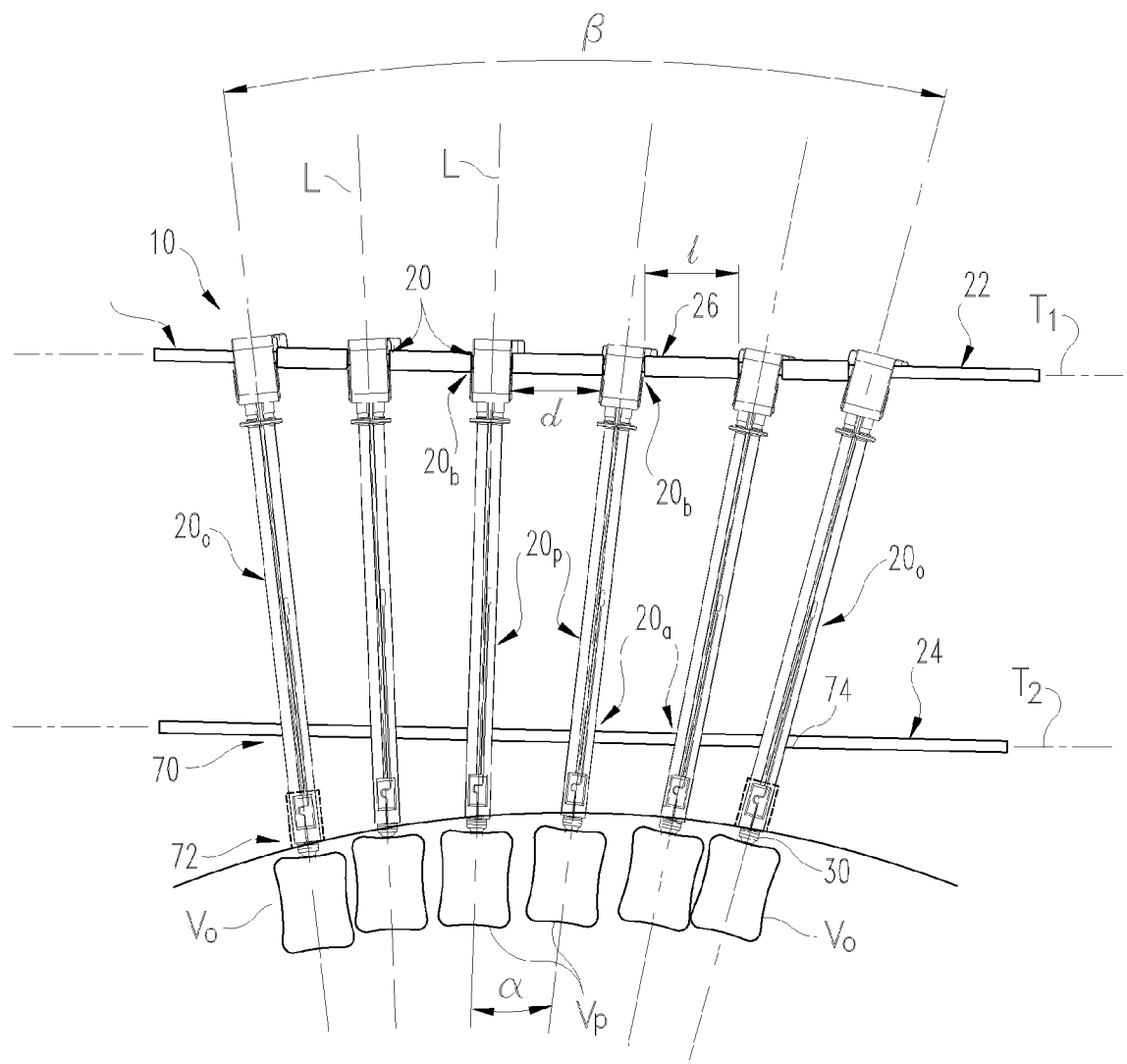
FIG. 3 is a schematical illustration of instrumentation for reducing a spinal deformity according to one form of the present invention.
Figure 7:
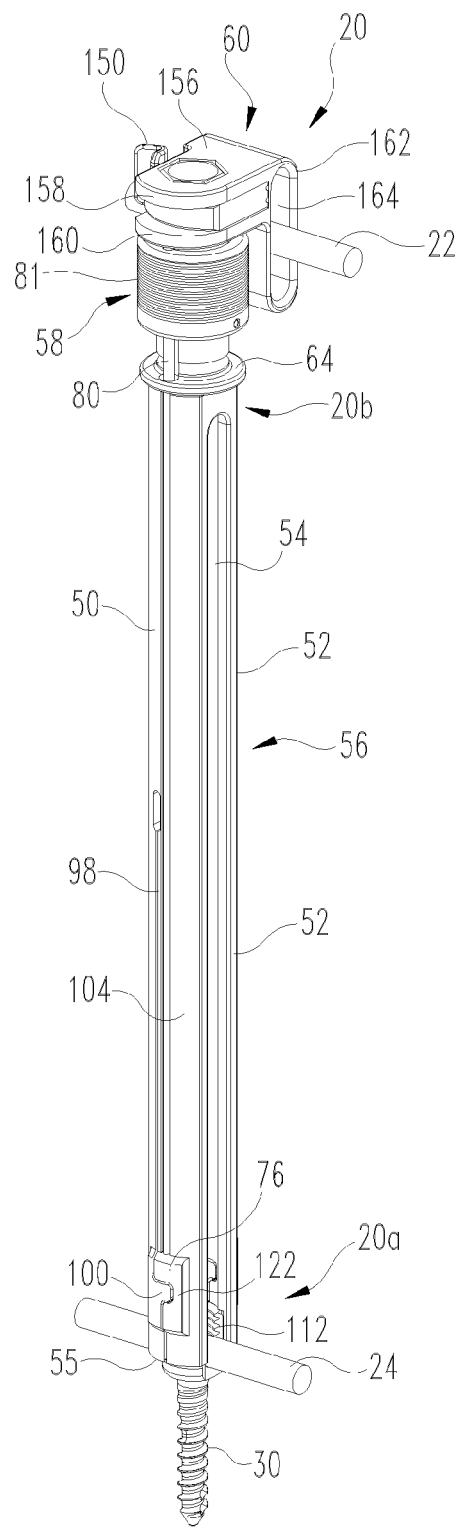
FIG. 7 is a perspective view of the elongate alignment element illustrated in FIG. 4.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Referring to FIGS. 1 and 2, shown therein is a scoliotic spine including a number of vertebrae V. In a scoliotic spine, the natural position and alignment of the vertebrae V are altered due to abnormal vertebral rotation (depicted by arrows R) and abnormal vertebral translation (depicted by arrows T). As a result, the anteroposterior axes A-P of the vertebrae V, which are normally positioned within a common plane P (i.e., the sagittal plane), are non-coplanar (i.e., extend along multiple planes). Additionally, in a scoliotic spine, the thoracic spine is typically lordotic, thereby resulting in abnormal divergence of the anteroposterior axes A-P of the thoracic vertebrae which is less than the physiological divergence of the normal spinal anatomy.

Referring to FIG. 3, shown therein is instrumentation 10 according to one form of the present invention for use in treatment of the spinal column, and more particularly to reduce a spinal deformity. As will be discussed below, in one embodiment, the instrumentation 10 is used to treat abnormal curvatures of the spinal column, such as, for example, scoliosis. However, it should be understood that the present invention may also be used to treat other spinal deformities, including kyphotic deformities and other abnormal spinal curvatures.

In one form of the invention, the instrumentation 10 is configured to reposition and/or realign the vertebrae V along one or more spatial planes toward their normal physiological position and orientation. Preferably, the spinal deformity is reduced systematically in all three spatial planes of the spine, thereby tending to reduce surgical times and provide improved results. Although the present invention is illustrated and described in association with treatment of the spinal column, and more specifically to reduce abnormal spinal curvatures such as scoliosis or kyphosis, it should be understood that the present invention may also be used to treat other anatomic structures, and may be used to treat other spinal deformities or abnormalities. In one embodiment, the instrumentation 10 is used to provide three-dimensional reduction of a spinal deformity via a posterior surgical approach. However, it should be understood that the instrumentation 10 may be used via other surgical approaches, including, a lateral approach, an anterior approach, a posterolateral approach, an anterolateral approach, or any other surgical approach. Additionally, although FIG. 3 illustrates use of the instrumentation 10 to reduce a convex portion of a spinal curvature, it should be understood that the instrumentation 10 may also be used to reduce a concave portion of a spinal curvature, or to reduce both convex and concave portions of a spinal curvature, which is typically the case with regard to treatment of scoliosis.

In the illustrated embodiment of the invention, the instrumentation 10 generally includes a plurality elongate alignment elements or extenders 20 adapted for coupling to a number of vertebrae, a elongate element or rod 22 extending between and engaged with the alignment elements 20, a elongate reduction element or rod 24 extending between and engaged with the alignment elements 20, and a plurality of spacer elements 26 of select lengths coupled between adjacent pairs of the alignment elements 20. As will be discussed below, the elongate alignment elements 20 are coupled to corresponding vertebrae V via a number of bone anchor elements 30, such as, for example, bone screws. See FIG. 13. The elements of the instrumentation 10 are each formed of a biocompatible material, such as, for example, stainless steel or titanium. However, other materials are also contemplated, including, for example, titanium alloys, metallic alloys such as chrome-cobalt, polymer based materials such as PEEK, composite materials, or any other suitable material that would occur to one of skill in the art. Further details regarding the structure and function of each of the elements associated with the instrumentation 10 will be set forth below.

The elongate alignment elements 20 each extend generally along a longitudinal axis L and include a proximal portion 20a adapted for coupling to a corresponding bone anchor 30 in vertebrae V and an opposite distal portion 20b. As used herein, the term "proximal portion" means the portion of the alignment element 20 extending toward the spinal column, and may encompass one-half or more of the overall length of the alignment element. Similarly, the term "distal portion" means the portion of the alignment element 20 extending away from the spinal column, which may likewise encompass one-half or more of the overall length of the alignment element. Accordingly, it should be understood that the term "proximal portion" is not limited to the proximal end portion of the alignment element, and the term "distal portion" is likewise not limited to the distal end portion of the alignment element. Additionally, although the longitudinal axes L along which the alignment elements 20 extend is illustrated as having a linear configuration, it should be understood that one or more of the longitudinal axes L may have a curved configuration, a curvilinear configuration, an angled configuration, a polygonal configuration, or any other suitable configuration. Furthermore, although the illustrated embodiment of the instrumentation 10 includes six alignment elements 20, it should be understood that the instrumentation 10 may includes any number of alignment elements 20.

In the form illustrated in FIG. 3, the elongate rod 22 extends generally along a first transverse axis $T_1$ and is engaged with the alignment elements 20 (as will be described in detail below), and the elongate reduction rod 24 extends generally along a second transverse axis $T_2$ and is likewise engaged with the alignment elements 20. The rod 22 is engaged with the distal portions 20b of the alignment elements 20 to maintain the distal portions 20b in general alignment along the first transverse axis $T_1$. The reduction rod 24 is axially displaced along the alignment elements 20 in a proximal direction from a position adjacent the distal portions 20b toward the proximal portion 20a, which in turn results in positioning of the proximal portions 20a in general alignment along the second transverse axis $T_2$. The alignment elements 20 act on the vertebrae V through the bone anchors 30 to reduce the spinal deformity via both translational and rotational movement of the vertebrae V, wherein the anteroposterior axes A-P of the vertebrae V are transitioned from an abnormal or non-coplanar state (FIG. 2) toward a corrected or coplanar state (see FIG. 28) wherein the anteroposterior axes A-P of the vertebrae V are positioned substantially within a common plane P, such as the sagittal plane.

Referring to FIGS. 4-11, shown therein is an elongate alignment element 20 according to one embodiment of the present invention in both assembled and unassembled views. As indicated above, each of the alignment elements 20 extends generally along a longitudinal axis L and includes a proximal portion 20a and a distal portion 20b. As will be described below, the alignment element 20 is configured for releasable coupling to a bone anchor 30 which is securely anchored to a vertebral bone V. When coupled to the bone anchor 30, a significant portion of the alignment element 20 extends outside of the patients body, thereby serving as an extension of the bone anchor 30, the purpose of which will be set forth below.

In the illustrated embodiment, the alignment element 20 has a generally cylindrical or tubular configuration including a pair of opposing outer walls 50, 52 surrounding a hollow interior or axial passage 53 and defining a generally circular cross section. However, it should be understood that other shapes and configurations of the alignment element 20 are also contemplated as falling within the scope of the present invention, including a solid rod-like configuration, an elliptical or oval shape, a rectangular shape, a diamond shape, a polygonal shape, or any other suitable shape or configuration. In the illustrated embodiment, the alignment element 20 further includes a slot 54 extending transversely there through and having a slot length $l_s$ extending generally along the longitudinal axis L between the proximal and distal portions 20a, 20b. The slot 54 has a slot width $w_s$ that is preferably equal to or slightly larger than an outer cross sectional dimension of the reduction rod 24. The slot 54 runs from approximately the distal portion 20b along the longitudinal axis L and terminates at an end 55 of the alignment element 20 located at the proximal portion 20a. Although the slot 54 has been illustrated and described as having a particular size and configuration, it should be understood that other sizes and configurations of the slot 54 are also contemplated as falling within the scope of the present invention.

As best illustrated in FIGS. 8-12, the alignment elements 20 include a main body 56, a locking pin assembly 58, and a locking cap 60. The main body 56 includes a shaft 62, a collar 64, and a slotted portion 65. The shaft 62 extends downwardly towards and terminates at an upper portion of the collar 64. The slotted portion 65 extends downwardly below the collar 64 and terminates at the end 55. The slotted portion 65 is defined by the two opposing side walls, 50, 52. An upper portion 66 of the shaft 62 defines a male engagement member 68 that is configured to be received within a female receptacle 70 located on the locking cap 60. In this form, the male engagement member 68 is configured in a hex shape, but other shapes are envisioned such star, square, triangular, and so forth. A lower portion 72 of the shaft 62 has a generally cylindrical shape and is configured to slidably receive the locking pin assembly 58. In one form, a portion 72 of the shaft 62 includes a pair of pin recesses 74 that run longitudinally along portion 72 to the collar 64 and then along outer walls 50, 52 to an interconnection member 76 located at approximately the end 55 of the outer walls 50, 52.

Figure 11:
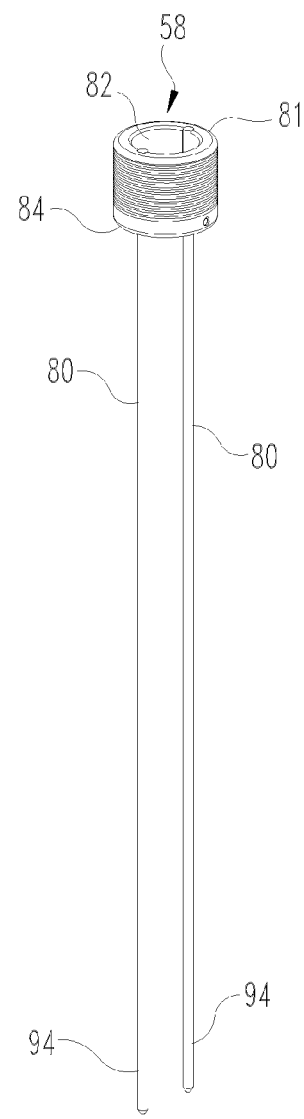
FIG. 11 is a perspective view of the locking pin assembly of the elongate element illustrated in FIG. 4.

In one form, the collar 64 includes a pair of apertures 78 running longitudinally through the collar 64 that are sized and configured to receive a pair of locking pins 80 of the locking pin assembly 58. As illustrated in FIG. 11, the pair of locking pins 80 extend longitudinally from and are connected to an adjustment member 81. The adjustment member 81 includes a passage or opening 82 that is sized and configured to slidably engage the lower portion 72 of the shaft 62 of the main body 56. Referring to FIGS. 4-7, when assembled the adjustment member 80 is operable to slide up and down the shaft 62 of the main body 56. After travelling downwardly so far, a lower portion 84 of the adjustment member 81 makes contact with an upper portion 86 of the collar 64 thereby preventing the adjustment member 81 from travelling any further along the shaft 62. In order to proper assemble the alignment element 20, the locking pins 80 are placed and travel in respective locking pin recesses 74 of the main body 56. In addition, the locking pins 80 are placed through and travel in the locking pin apertures 78 located on the collar 64.

A lower segment 90 of the slotted portion 65 includes the interconnection element 76. The interconnection segment 76 extends outwardly and away from the slotted portion 65 of the main body 56 and includes a pin passage 92 that runs longitudinally through at least a portion of the interconnection segment 76. In one form, the interconnection segment 76 has a larger outside diameter than outside walls 50, 52. The pin passage 92 is sized and configured to receive an end portion 94 of the locking pins 80. As illustrated best in FIGS. 4 and 8, each outer wall 50, 52 of the slotted portion 65 includes a cutout 98 that runs from the end 55 of each outer wall 50, 52 to approximately the center of the slotted portion 65. At the interconnection segment or element 76, the cutout 98 is oriented and shaped to define a male member 100 that is configured to be received in a female member 102 formed in the interconnection segment 76. The pin passages 92 in the interconnection segment 76 run through both the male and female members 100, 102. As further illustrated in FIG. 4, an upper portion 101 of the interconnection segment 76 may also define a second locking member through which the pins 80 may be inserted. The second locking member 101 also includes the pin passage 92 for receiving the pins 80.

Figure 12:
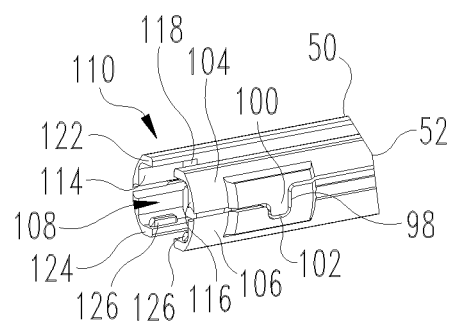
FIG. 12 is a perspective view of a portion of the main body of the elongate element illustrated in FIG. 4 depicting a bone anchor receptacle in the main body.

The cutouts 98 in each outer wall 50, 52 allow a first and second lower portion 104, 106, defined by each respective cutout 98, of the slotted portion 65 of the main body 56 to flex outwardly and away from one another when the pins 80 of the locking pin assembly 58 are not positioned in the pin passages 92 of the interconnection segments 76. Referring to FIG. 12, a bone anchor receptacle 108 is included in an interior end 110 of the slotted portion 65 of the main body 56. As the bone anchor 30 is inserted into the bone anchor receptacle 108, the first and second lower portions 104, 106 of each respective wall 50, 52 flex outwardly thereby allowing at least a portion of a head 112 of the bone anchor 30 to pass into or be received by the bone anchor receptacle 108.

The bone anchor receptacle 108 includes a first side wall 114 formed in the first wall 50 and a second side wall 116 formed in the second wall 52. A back interior wall 118 is formed in both the first and second walls 50, 52 for engaging an upper segment 120 of the head 112 of the bone anchor 30. The bone anchor receptacle 108 further includes an upper side wall 122 formed by a portion of the first and second walls 50, 52 and a lower side wall 124 formed by a portion of the first and second walls 50, 52. In one form, the lower side walls 124 each include a tapered protrusion 126 extending upwardly into the bone anchor receptacle 108. The tapered protrusions 126 are sized to fit within a pair of anchor recessed portions 128 of the bone anchors 30 to help secure the head 112 of the bone anchor 30 into the bone anchor receptacle 108. In the illustrated form, the bone anchor receptacle 108 has a generally rectangular shape, but other shapes may be utilized in other forms.

Figure 13:
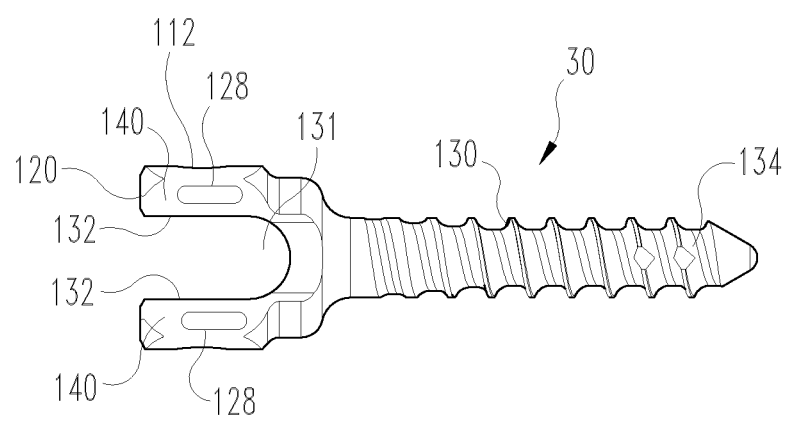
FIG. 13 is a side view of a representative bone anchor.
Figure 14:
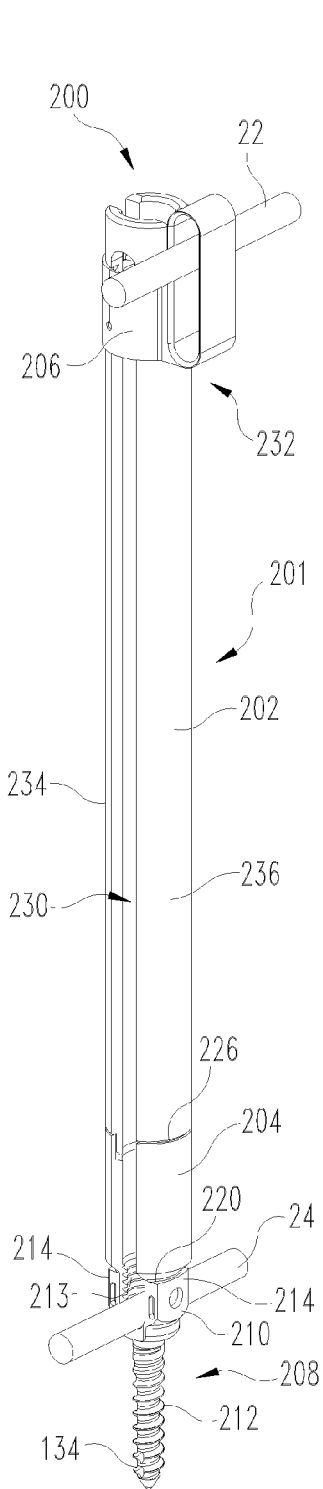
FIG. 14 is a perspective view of another representative elongate alignment element according to another form of the present invention.
Figure 15:
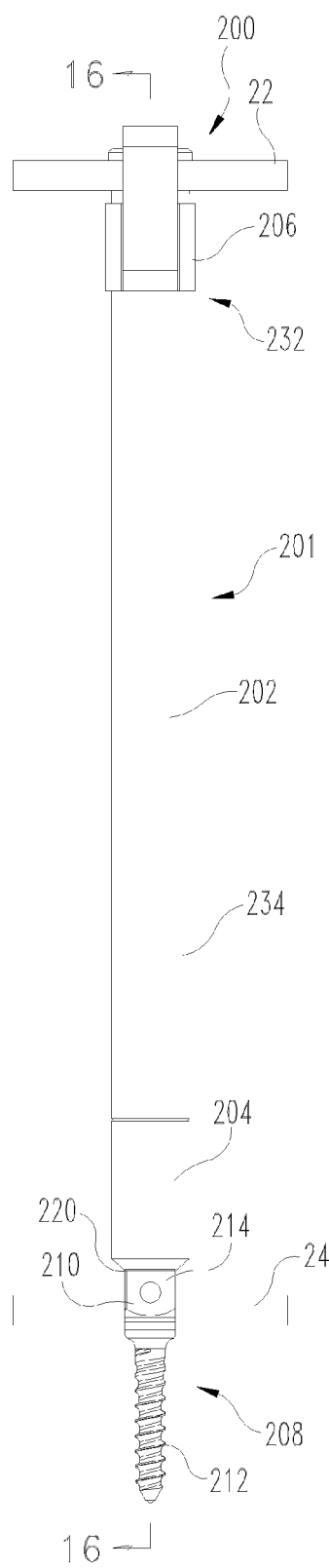
FIG. 15 is a side view of the elongate alignment element illustrated in FIG. 14.

Referring to FIG. 13, a representative form of a bone anchor 30 that can be utilized in conjunction with the instrumentation 10 is illustrated. The bone anchor 30, which in this form comprises a pedicle screw, includes a screw head 112 and a threaded shaft 130 extending downwardly from the screw head 112. As illustrated, the screw head 112 comprises a U-shaped receiver or cradle 131 that is defined by two opposing internally threaded sidewalls 132. In one form, bone anchor 30 is preferentially made from titanium and comprises a top-loading screw. In this form, the threaded shaft 130 of the bone anchor 30 is inserted into the vertebrae V as set forth above in FIG. 3. In one form, the bone anchor 30 has a self-tapping flute 134 that obviates the need for tapping. However, in cases of dense, sclerotic, or osteoporotic bone, tapping is often recommended prior to insertion of the bone anchor 30. As previously set forth, in this form each of the sidewalls 132 includes an anchor recessed portion 128 that is sized and configured to receive the tapered protrusions 126 of the bone anchor receptacle 108 once the bone anchor 30 is positioned in the bone anchor receptacle 108.

During operation, once the bone anchors 30 are placed in vertebrae V (see FIG. 3), the bone anchor receptacle 108 is positioned around at least a portion of the head 112 of the bone anchor 30. Referring to FIGS. 4-7, in this form when the bone anchor receptacle 108 of the main body 56 is positioned on the head 112 of the bone anchor 30, the locking pin assembly 58 is in an open or unlocked state thereby allowing the first and second lower portions 104, 106 of each respective wall 50, 52 to flex outwardly allowing at least a portion of the head 112 of the bone anchor 30 to pass into the bone anchor receptacle 108. Once the head 112 of the bone anchor 30 is in the bone anchor receptacle 108, the anchor recessed portions 128 of the bone anchor 30 receive the tapered protrusions 126 of the bone anchor receptacle 108. In one form, this arrangement at least partially secures the alignment element 20 to the bone anchor 30.

To further secure the alignment element 20 to the bone anchor 30, the locking pin assembly 58 is placed in a locked or closed state. In the locked or closed state, the first and second lower portions 104, 106 of each respective wall 50, 52 are not permitted to flex outwardly thereby causing the bone anchor receptacle 108 to clamp or fixedly secure the bone anchor 30 in the bone anchor receptacle 108. The first and second lower portions 104, 106 of each wall 50, 52 flex outwardly because the tapered protrusions 126 of the bone anchor receptacle 108 make contact with respective outside surfaces 140 of the head 112 of the bone anchor 30 prior to being received in the anchor recessed portions 128 thereby forcing the first and second lower portions 104, 106 to flex outwardly.

Once the tapered protrusions 126 are received in the anchor recessed portions 128, the bone anchor receptacle 108 returns to a normal or un-flexed state. In the flexed state, the passages 92 running through the male and female portions 100, 102 of the interconnection element 76 are misaligned thereby preventing the end portions 94 of the pins 80 of the locking pin assembly 58 from being received in the passages 92 of the male and female portions 100, 102 of the interconnection element 76. In the normal or un-flexed state, the passages 92 in the male and female portions 100, 102 of the interconnection element 76 are aligned with one another thereby allowing the pins 80 of the locking pin assembly 58 to be inserted into the respective passages 92. The pins 80 are inserted into the passages 92 by moving the adjustment member 81 downwardly toward the collar 64 along the shaft 62. Once the adjustment member 81 of the locking pin assembly 58 reaches the collar 64, the collar 64 prevents further movement of the locking pin assembly 58 and the bone anchor 30 is fixedly secured in the bone anchor receptacle 108 of the alignment element 20. The pins 80 prevent the male and female portions 100, 102 of the interconnection element 76 from separating thereby preventing the first and second lower portions 104, 106 from flowing outwardly. The pins 80 are removed from the passages 92 by moving the adjustment member 81 upwardly along the shaft 62 thereby allowing the bone anchor 30 to be removed from the bone anchor receptacle 108.

Figure 9:
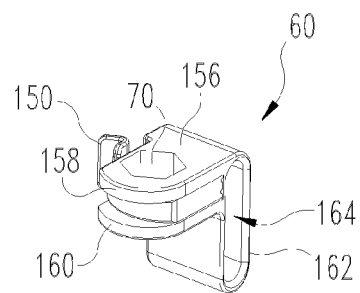
FIG. 9 is a perspective view of the locking cap of the elongate element illustrated in FIG. 4.
Figure 10:
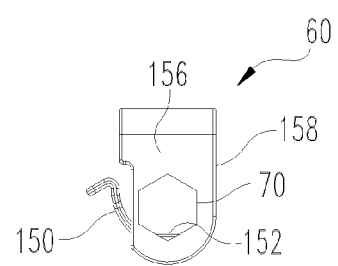
FIG. 10 is a top view of the locking cap of the elongate element illustrated in FIG. 4.
Figure 8:
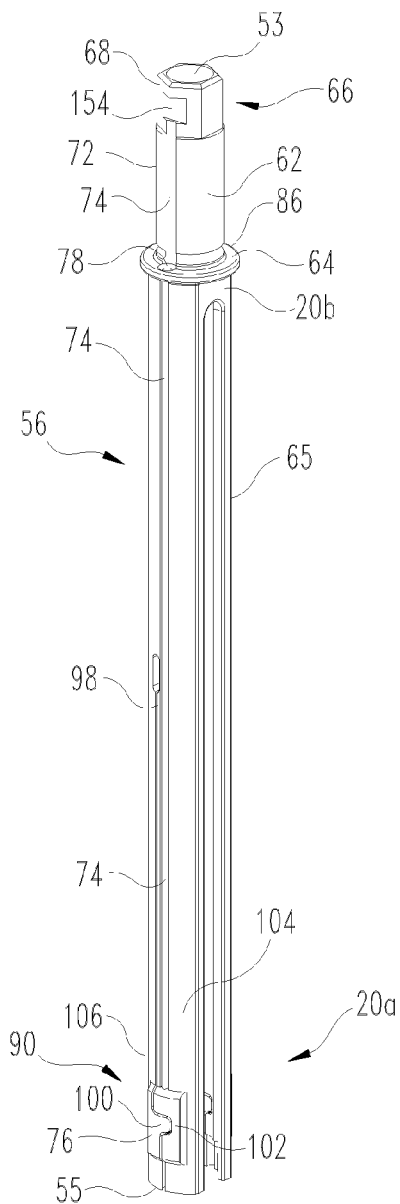
FIG. 8 is a perspective view of the main body of the elongate element illustrated in FIG. 4.

Referring to FIGS. 4-10, as previously set forth the alignment element 20 also includes a locking cap 60. The locking cap 60 prevents the locking pin assembly 58 from being removed from the shaft 62 and secures the rod 22 to the alignment element 20. When the locking cap 60 is removed from the main body 56, the locking pin assembly 58 is capable of being removed from the main body 58 by sliding the locking pin assembly 58 off of the shaft 62. Referring to FIGS. 8-10, the locking cap 60 includes a lever 150 that is configured and operable to fixedly secure the locking cap 60 to the main body 56. In particular, the locking cap 60 is secured to the male engagement member 68 of the upper portion 66 of the main body 56.

As previously set forth, the upper portion 66 of the main body 56 includes a male engagement member 68 that is sized to fit within a female receptacle 70 of the locking cap 60. To secure the locking cap 60 to the main body 56, the lever 150 is moved outwardly or counterclockwise so that a locking tab 152 of the locking cap 60 is no longer exposed in the female receptacle 70 (see FIG. 10). At this point, the locking cap 60 is slid onto the male engagement member 68 and the lever 150 is released. A retaining slot 154 is included on both sides of the male engagement member 68 in which the tab 152 becomes positioned when the lever 150 is released thereby securing the locking cap 60 to the male engagement member 68 of the main body 56.

The female receptacle 70 of the locking cap 60 is positioned on a tongue 156 of the locking cap 60. The tongue 156 includes an upper segment or portion 158 and a lower segment or portion 160 separated by the lever 150. Extending downwardly from a rear portion of the tongue 156 is a retaining member 162 that includes a rod passage or opening 164 that is sized and configured to receive the rod 22. In this form, the retaining member 162 and rod passage 164 have a generally oval shape, but other shapes are envisioned. During assembly, the locking cap 60 is positioned on the male engagement member 68 such that the rod passage 164 runs parallel with the slot 54 in the main body 56 (see FIG. 6). In this arrangement, the first rod 22 and the reduction rod 24 lie along substantially parallel longitudinal axes with one another.

Referring to FIGS. 14-19, yet another representative elongate alignment element 200 is illustrated that can be utilized by the present invention. In this form, the alignment element 200 is manufactured to include a main body 201 that includes a bone anchor 208. In particular, the bone anchor 208 is formed as an integral part of the main body 201. As set forth in greater detail below, a breaking point 220 is included where the main body 201 is connected with the bone anchor 208 that allows the main body 201 to be broken away from the bone anchor 208. Since the bone anchor 208 is formed as an integral part of the main body 201, during surgery the bone anchor 208 is implanted in the vertebra V while attached to the main body 201. However, as would be appreciated by one skilled in the art, all other aspects of the use of this respective form of the present invention remain substantially the same.

Figure 16:
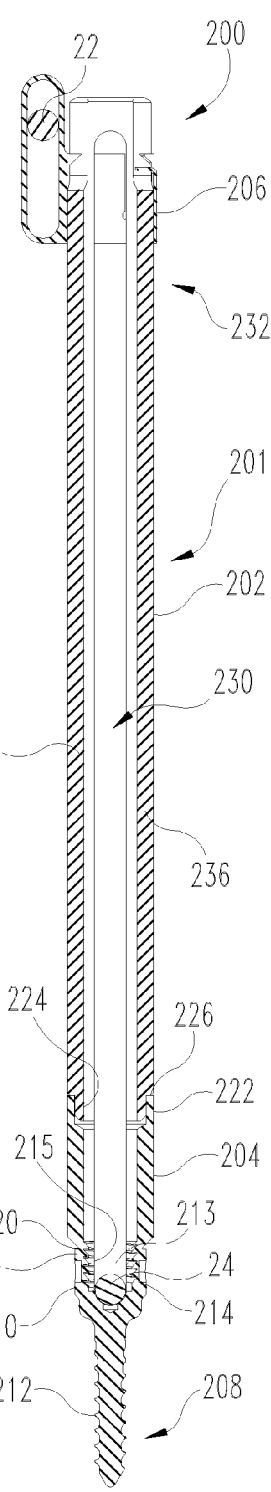
FIG. 16 is a cross-sectional view of the elongate alignment element shown in FIG. 14, as viewed along line 16-16 of FIG. 15.

In one form, the alignment element 200 includes a main body 201 that comprises an upper body 202 and a lower body 204, but in other forms the main body 201 may constitute a single integral component. Further, the alignment element 200 includes a cap 206 and a bone anchor 208. The bone anchor 208 is formed as an integral part of the lower body 204. The bone anchor 208, which in this form comprises a pedicle screw, includes a screw head 210 and a threaded shaft 212 extending downwardly from the screw head 210. As illustrated, screw head 210 comprises a U-shaped receiver or cradle 213 that includes two opposing internally threaded sidewalls 214. In this form, the threaded shaft 212 of the bone anchor 208 is inserted into the vertebrae V. In particular, a tool is used to secure the bone anchor 208 to the vertebrae V while the bone anchor 208 is attached to the main body 201. In one form, the bone anchor 208 has a self-tapping flute 134 that obviates the need for tapping. However, in cases of dense, sclerotic, or osteoporotic bone, tapping is often recommended prior to insertion of the bone anchor 208. The bone anchor 208 and lower body 204 are connected to one another at a lower break point 220. As illustrated in FIG. 16, in one form each side wall 214 includes an internal thread 215 that runs above the lower break point 220. As set forth in greater detail below, once the vertebrae V are properly aligned and the second reduction rod 24 is properly positioned in the receiver 213 of the bone anchor 208, the lower break point 220 is utilized to remove the main body 201 from the bone anchor 208.

As set forth above, in this representative form the main body 201 comprises an upper body 202 that is connected with a lower body 204. As illustrated in FIG. 16, the lower body 204 includes a female engagement segment 222 that receives a male engagement segment 224 of the upper body 202. In particular, the male engagement segment 224 is slid into the female engagement segment 222. In one form, once the male engagement segment 224 is positioned within the female engagement segment 222, the upper body 202 and the lower body 204 are welded together along a weld line 226.

Figures 17, 18:
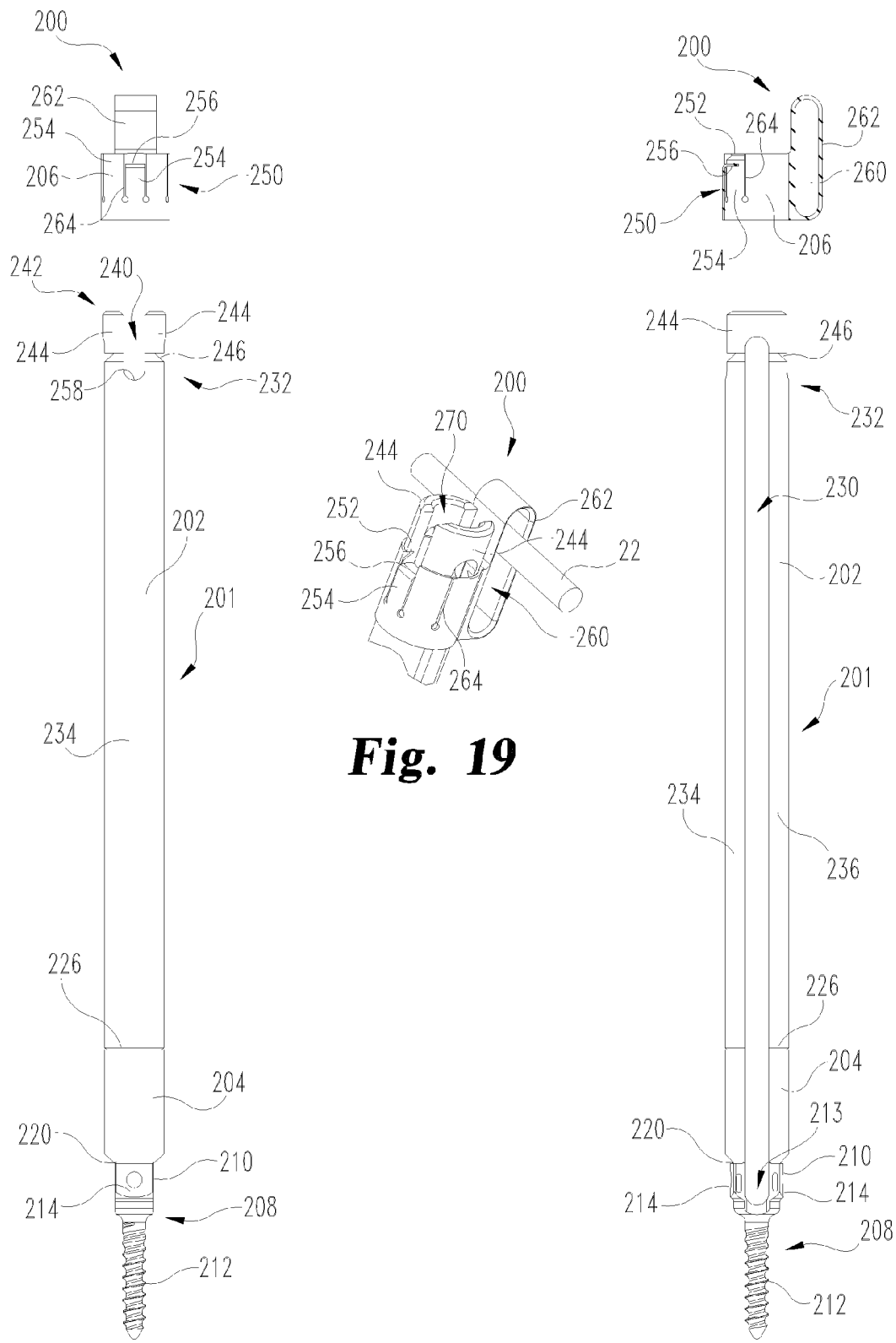
FIG. 17 is another side view of the elongate alignment element shown in FIG. 14 with a cap removed.
FIG. 18 is another side view of the elongate alignment element shown in FIG. 14 with the cap removed.

Referring to FIG. 18, the main body 201 includes a first slot 230 that runs along a first longitudinal axis from a distal end 232 of the main body 201 to the receiver 213 of the bone anchor 208. As set forth in greater detail below, the reduction rod 24 is configured and operable to travel in the first slot 230 from the distal end 232 of the main body 201 into the receiver 213 of the bone anchor 208. The first slot 230 in the main body 201 defines a first leg or wall 234 and a second leg or wall 236 in the main body 201. The first slot 230 defines an opening through the main body 201 through which the reduction rod 24 is inserted.

As illustrated in FIG. 17, if the main body 201 is rotated along its longitudinal axis a second slot 240 is included in an upper portion 242 of the main body 201. In this form, the second slot 240 is located spaced apart from the first slot 230 or approximately 90° from a central longitudinal axis of the first slot 230. The second slot 240 is include on both sides of the main body 201 and defines two opposing side walls 244 in the upper portion 242 of the main body 201. The two opposing side walls 244 include an upper break point 246 that allow at least a portion of the upper opposing side walls 244 to break off or away from the main body 201 during disassembly of the instrumentation 10. In one form, once the side walls 244 are broken away from the main body 201, the cap 206 is capable of being removed from the main body 201. Further, once the two opposing side walls 244 are removed from the main body 201, the first and second opposing walls 234, 236 defined by the first slot 230 can be broke away from the head 210 of the bone anchor 208 along the lower break point 220.

In one form, the upper break point 246 is formed as a groove in the opposing side walls 244. The cap 206 is sized and configured to slide over at least the upper portion 242 of the main body 201. A portion of the cap 206 defines a collet 250 that is configured to secure the cap 206 to the main body 201. As the collet 250 travels downwardly on the upper portion 242 of the main body 201 at least one protrusion 252 on a section 254 of the collet 250 is configured to fit within the groove defined by the upper break point 246. In one form, the collet 250 includes two protrusions 252 defined in the section 254 of the collet 250. This removably secures the cap 206 to the main body 201 of the alignment member 200. In addition, an alignment tab or member 256 in a respective section 254 of the collet 250 is sized and configured to fit within an end 258 of the second slot 240. The alignment tab 256 prevents rotational movement of the cap 206 about the longitudinal axis of the main body 201 when the alignment tab 262 is positioned in the second slot 240. The section 254 of the collet 250 selected for the alignment tab 256 is configured such that a rod passage or opening 260 in a retaining member 262 of the cap 206 lies on a substantially parallel longitudinal axis as the first slot 230 of the main body 201. The sections 254 of the collet 250 are defined by a plurality of slots 264 in the cap 206. As illustrated in FIGS. 16 and 19, the main body 201 of the alignment element 200 is configured to include a central passage 270 along the longitudinal axis of the main body 201.

Having illustrated and described the elements and features associated with the instrumentation 10, reference will now be made to a method for reducing a spinal deformity according to one form of the present invention. Referring to FIG. 20, shown therein are bone anchors 30 engaged to a vertebra V in a bilateral arrangement along each side of the spinal column. In the illustrated embodiment, a pair of bone anchors 30a, 30b is anchored to a single vertebra V. However, it should be understood that a pair of bone anchors 30a, 30b is engaged to each of a plurality of vertebrae V along the portion of the spinal column being treated. It should further be understood that in other embodiments, a single bone anchor 30 or three or more bone anchors 30 may be engaged to each of a plurality of vertebrae V along the portion of the spinal column being treated.

In the illustrated embodiment of the invention, the bone anchors 30 are configured as bone screws having a threaded shank portion 130 and a head portion 112. In one embodiment of the invention, the bone screws are configured as pedicle screws, wherein the threaded shank portion 130 has a length and a thread configuration suitable for engagement within the pedicle region of the vertebra V. In the illustrated embodiment of the bone anchor 30, the head portion 112 is configured for engagement with the rod 24. In one specific embodiment, the head portion 112 defines a passage 131 sized to receive a spinal rod therein, with a fastener or setscrew extending through the head portion 112 and into engagement with the spinal rod 24 to capture and secure the spinal rod 24 within the passage 131. Additionally, the head portion 112 includes a pair of spaced apart arms 132 defining an open end which provides the head portion 112 with a top-loading, U-shaped configuration, with the fastener or setscrew engaged with internal threads formed along the spaced apart arms 132. Further details regarding bone screws having a configuration similar to that of the bone screws illustrated and described, for example, in U.S. Pat. No. 6,783,527 to Drewry et al., the contents of which are incorporated herein by reference.

However, it should be understood that other types and configuration of bone screws are also contemplated for use in association with the instrumentation 10, including, for example, bone screws having a closed head portion or a head portion defining a side-loading, C-shaped configuration. Additionally, other embodiments of bone screws are also contemplated which include a head portion configured as an unthreaded stem or shaft, with the spinal rod coupled to the unthreaded stem via a connector or coupling mechanism, an example of which is illustrated and described in U.S. Pat. No. 5,643,263 to Simonson or U.S. Pat. No. 5,947,967 to Barker, the contents of each patent reference incorporated herein by reference.

In still other embodiments of the invention, bone screws may be used in association with the instrumentation 10 which allow the head portion to be selectively pivoted or rotated relative to the threaded shank portion along multiple planes or about multiple axes. In one such embodiment, the head portion includes a receptacle for receiving a spherical-shaped portion of a threaded shank therein to allow the head portion to pivot or rotate relative to the threaded shank portion. A locking member or crown may be compressed against the spherical-shaped portion via a set screw or another type of fastener to lock the head portion at a select angular orientation relative to the threaded shank portion. Further details regarding one type of multi-axial screw suitable for use in association with the present invention are illustrated and described, for example, in U.S. Pat. No. 5,797,911 to Sherman et al., the contents of which are hereby incorporated herein by reference. The use of multi-axial bone anchors may be beneficial for use in the lower lumbar region of the spinal column, and particularly below the L4 vertebrae, where lordotic angles tend to be relatively high compared to other regions of the spinal column.

It should be understood that the bone screw embodiments illustrated and described herein are exemplary, and that other types and configurations of bone screws may also be used in association with the present invention, the likes of which would be apparent to one of ordinary skill in the art. It should also be understood that other types and configuration of bone anchors may be used in association with the present invention, including, for example, spinal hooks configured for engagement about a portion of a vertebra, bolts, pins, nails, clamps, staples and/or other types of bone anchor devices capable of being anchored in or to vertebral bone.

Referring to FIG. 21, shown therein is another embodiment of the invention wherein the alignment element 20, is connected directly to a set of the bone screws 30a, 30b anchored along one side of the spinal column, and more specifically to the head portion 112 of the bone screws, to couple the alignment elements 20, to the vertebrae V in the manner described above. Referring now to FIGS. 22-27, shown therein are schematical illustrations of various stages of correction of an abnormal spinal curvature using the instrumentation 10. Although the alignment elements 20 are each shown as being positioned along a central or medial portion of the vertebrae V (as illustrated and described above with regard to FIGS. 20-21), it should be understood that the alignment elements 20 may alternatively be positioned along either or both sides of the vertebrae V. It should further be understood that positioning of the alignment elements 20 along other portions of the vertebrae V is also contemplated as falling within the scope of the present invention. Additionally, although FIGS. 22-27 make specific reference to alignment elements 20, it should be understood that use of the alignments elements 200 or other embodiments of alignment elements is also contemplated as falling within the scope of the present invention.

Figure 22:
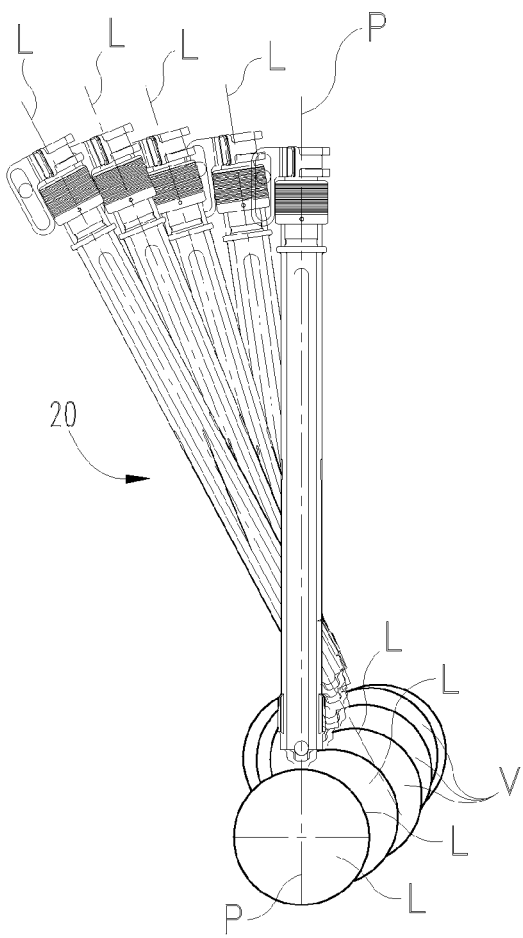
FIG. 22 is a schematical illustration of the scoliotic spine shown in FIG. 2 with the anteroposterior axes of the vertebra positioned in an abnormal, non-coplanar state, and with alignment elements engaged to the vertebra and arranged generally along the anteroposterior axes.

Referring initially to FIG. 22, shown therein is a number of the alignment elements 20 coupled to a corresponding number of vertebrae V. As indicated above, the alignment elements 20 may be engaged directly to a series of bone anchors 30 anchored along one side of the spinal column, or may be engaged to a bridge or link member extending between a pair of bilaterally-positioned bone anchors 30 anchored along each side of a corresponding vertebra. As also indicated above, the alignment elements 20 may alternatively be engaged directly to the vertebrae V.

As discussed above with regard to FIGS. 1 and 2, in a scoliotic spine, the natural physiological position and alignment of the vertebrae V are altered due to abnormal vertebral rotation and translation. As a result, the anteroposterior axes A-P of the vertebrae V, which are normally positioned within a common plane P (i.e., the sagittal plane), extend along multiple planes in a non-coplanar state. Additionally, in a scoliotic spine, the thoracic region of the spine is typically lordotic, thereby resulting in divergence between the anteroposterior axes A-P which is less than normal physiological divergence. Referring once again to FIG. 22, the alignment members 20 are initially positioned and arranged such that the longitudinal axes L of the alignment members 20 are positioned is substantial co-axial alignment with the non-corrected anteroposterior axes A-P of the vertebrae V. As a result, the longitudinal axes L of the alignment members 20 are initially not in alignment with one another along a common plane P, but instead extend along multiple planes in a non-coplanar configuration.

Figure 23:
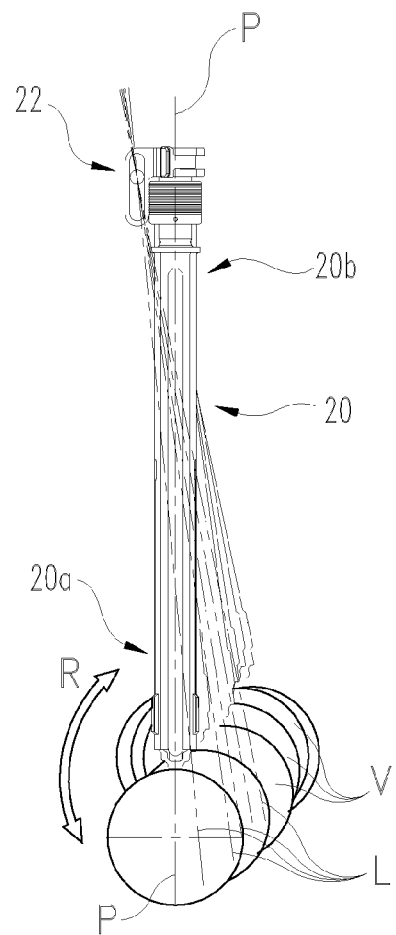
FIG. 23 is a schematical illustration of the alignment elements shown in FIG. 22, with a first rod engaged to the locking caps of the alignment elements to align the distal portions generally along the transverse axis of the first reduction element and resulting in derotation of one or more of the vertebrae toward a corrected state.

Referring to FIG. 23, the distal portions 20b of the alignment elements 20 are drawn together in general alignment with one another and the first rod 22 is inserted through the distal end portions of each of the passages 164 in the locking cap 60 of the alignment elements 20. In order to facilitate alignment of the distal portions 20b with one another, the alignment elements 20 may be manually grasped and manipulated by the surgeon and/or an instrument or tool may be used to exert a lateral or torsional force onto one or more of the alignment elements 20. However, in another embodiment, general alignment of the distal portions 20b with one another may be accomplished by inserting the rod 22 into central portions of the passages 164, which may initially be in closer alignment with one another compared to the distal end portions of the slots 54. Once inserted into the central portions of the passages 164, the first rod 22 may be axially displaced through the passages 164 in a distal direction, which in turn draws the distal portions 20b of the alignment elements 20 into general alignment with one another via the exertion of lateral forces onto the inner side surfaces of the passages 164. Various instruments may be used to facilitate axial displacement of the first rod 22 through the passages 164, the likes of which will be discussed in greater detail below with regard to the reduction rod 24. In some forms, initial introduction of the first rod 22 into the passages 164 may be facilitated via the use of a surgical mallet, a slap hammer, or by any other suitable tool or instrument.

The first rod 22 cooperates with the alignment elements 20 to maintain alignment of the distal portion 20b generally along the first transverse axis $T_1$ (FIG. 3), with the first transverse axis $T_1$ preferably extending along the sagittal plane P. Alignment of the distal portions 20b of the alignment elements 20 generally along the first transverse axis $T_1$ correspondingly imparts rotational movement to one or more of the alignment elements 20. Rotation of the alignment elements 20 in turn imparts a rotational force onto the corresponding vertebrae V to derotate the vertebrae V generally along the transverse plane in the direction of arrow R. It should be understood that the direction of derotation is dependent on the particular characteristics of the spinal deformity being treated, and may occur in a clockwise direction and/or a counter-clockwise direction. It should further be understood that bringing the distal portions 20b into general alignment with one another may not result in rotation of one or more of the alignment elements 20, in which case the corresponding vertebrae V will not be rotationally affected. Although alignment of the distal portions 20b of the alignment elements 20 partially reduces the spinal deformity, further correction is required.

Figure 24:
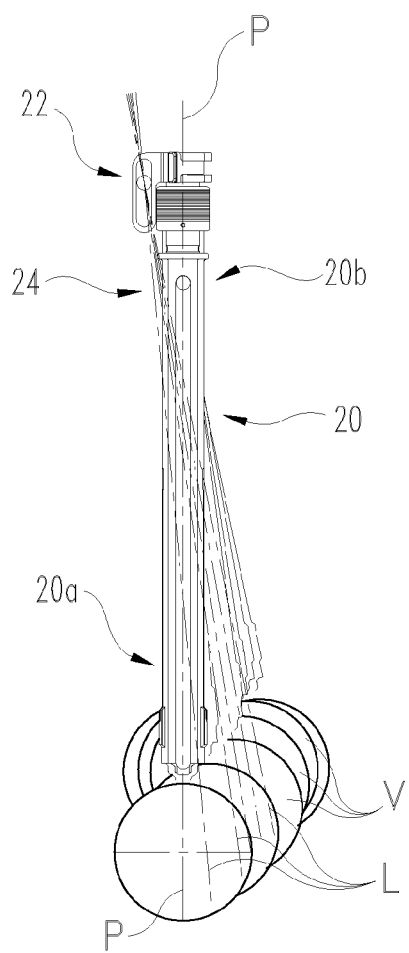
FIG. 24 is a schematical illustration of the alignment elements shown in FIG. 23, with a reduction rod engaged to the distal portions of the alignment elements.

Referring to FIG. 24, the reduction rod 24 is inserted through the distal end portions of each of the slots 54 in the alignment elements 20. Since the distal end portions of the slots 54 are maintained in general alignment with one another via the first rod 22, insertion of the reduction rod 24 into the slots 54 should not require significant manipulation of the alignment elements 20. However, introduction of the reduction rod 24 into the slots 54 may be facilitated via the use of a surgical mallet, a slap hammer, or by any other suitable tool or instrument.

Figure 25:
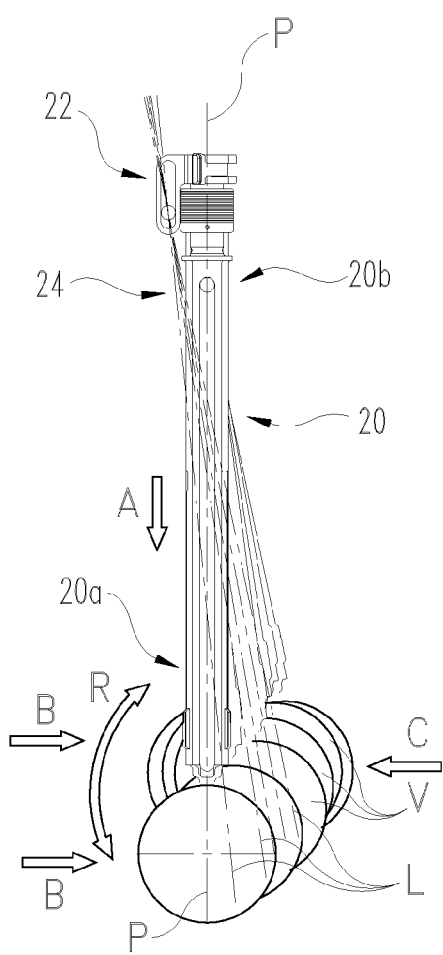
FIG. 25 is a schematical illustration of the alignment elements shown in FIG. 24, showing sliding engagement of the reduction rod along the alignment elements in a proximal direction to translate and derotate one or more of the vertebrae toward a corrected state.

Referring now to FIG. 25, with the first rod 22 remaining in a substantially stationary position to maintain the distal portions 20b in general alignment with one another, the reduction rod 24 is proximally displaced through the slots 54 in the alignment elements 20 in the direction of arrow A, away from the first rod 22 and generally along the plane P. Displacement of the reduction rod 24 through the slots 54 may be facilitated via the use of a surgical mallet, a rod pusher or persuader, a distractor device engaged between the reduction rod 24 and another element to distract the reduction rod 24 in a proximal direction away from the first rod 22, or by any other suitable tool or instrument. The tools or instruments used to displace the reduction rod 24 through the slots 54 may be manually driven or may be powered. Additionally, the tools or instruments may be incrementally advanced in a controlled manner to provide incremental displacement of the reduction rod 24 through the slots 54 in the alignment elements 20. Such incremental advancement may be provided by way of a rack-and-pinion type drive, a ratcheting drive, a turnbuckle mechanism, or by any other suitable drive or advancement mechanism.

Sliding engagement of the reduction rod 24 through the slots 54 in turn draws the alignment elements 20 toward one another via the exertion of lateral forces onto the inner side surfaces of the alignment elements 20. Specifically, as the reduction rod 24 is proximally displaced through the slots 54, one or more of the alignment elements 20 is correspondingly rotated about the first rod 22 toward the sagittal plane P. Rotation of the alignment elements 20 in turn imparts a rotational force onto the corresponding vertebrae V to provide further derotation of the vertebrae V generally along the transverse plane in the direction of arrow R which, as discussed above, may occur in a clockwise direction and/or a counter-clockwise direction.

Additionally, sliding engagement of the reduction rod 24 through the slots 54 (and rotation of the alignment elements 20 about the first rod 22) also imparts a lateral force onto the corresponding vertebrae V, which in turn results in relative translational movement of the vertebrae V generally along the coronal plane in the directions of arrow B and/or arrow C. It should be understood that the direction of translational movement of the vertebrae V is dependent on the particular spinal deformity being treated, and may occur in either or both of the directions of arrows B and C. It should also be understood that proximal displacement of the second rod 24 through the slots 54 may not result in rotation of one or more of the alignment elements 20, in which case the corresponding vertebrae V will not be rotationally or translationally affected. It should further be understood that derotation of the vertebrae V in the direction of arrow R and translation of the vertebrae V in the direction of arrows B and C results in a reduction of the misalignment of the vertebrae V along both the transverse and coronal planes.

Referring to FIG. 26, further proximal displacement of the reduction rod 24 through the slots 54 in the alignment elements 20 results in additional derotation of the vertebrae V generally along the transverse plane in the direction of arrow R, and additional translation movement of the vertebrae V generally along the coronal in the directions of arrows B and C. Referring to FIG. 27, the reduction rod 24 is further displaced through the slots 54 until the reduction rod 24 becomes positioned in the receiver 131 of the bone anchor 30. In this position, the proximal portions 20a are drawn into general alignment with one another along the second transverse axis $T_2$, with the second transverse axis $T_2$ preferably arranged and extending generally along the sagittal plane P. With the distal portions 20b of the alignment elements 20 maintained in general alignment along the transverse axis $T_1$ via the first rod 22, and with the proximal portions 20a drawn into general alignment with one another along the second transverse axis $T_2$ via displacement of the reduction rod 24, the longitudinal axes L of the alignment elements 20 are resultingly positioned in general alignment with one another in a co-planar relationship along the sagittal plane P. General alignment of the alignment elements 20 along the sagittal plane P in turn results in general alignment of the anteroposterior axes A-P of the vertebrae V along the sagittal plane P, thereby reducing the spinal deformity via correcting misalignment of the vertebrae V along both the coronal and transverse planes.

With the outer vertebrae Vo positioned at the correct physiological height and anatomic angle, positioning of the remaining vertebrae V into correct alignment along the sagittal plane is accomplished via engagement of the spacer elements 26 between adjacent pairs of alignment elements 20p. As indicated above, the spacer elements 26 may be provided with a fixed configuration defining a select spacer length l, or may be provided with a variable configuration wherein the overall length of the spacer may be adjusted to a select spacer length l, either pre-operatively or intra-operatively. In either case, the spacer elements 26 are engaged between the distal portions 20b of adjacent pairs of the elongate alignment elements 20p to space the adjacent distal portions 20b apart at a select distance d. With the proximal portions 20a of the adjacent pair of alignment elements 20p securely coupled to the adjacent vertebrae Vp, spacing the distal portions 20b apart at a select distance d correspondingly positions the adjacent pairs of vertebrae Vp at an angle α, substantially corresponding to the normal physiological angular orientation of the adjacent vertebrae Vp along the sagittal plane.

Although various embodiments have been described as having particular features and/or combinations of components, other embodiments are possible having a combination of any features and/or components from any of embodiments as discussed above. As used in this specification, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the terms "proximal" and "distal" refer to the direction closer to and away from, respectively, an operator (e.g., surgeon, physician, nurse, technician, etc.) who would insert the medical implant and/or instruments into the patient. For example, the portion of a medical instrument first inserted inside the patient's body would be the distal portion, while the opposite portion of the medical device (e.g., the portion of the medical device closest to the operator) would be the proximal portion.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. An alignment apparatus for use in correction of a deformity, comprising:
    an elongate alignment element extending along a first longitudinal axis and including a proximal portion and a distal portion, wherein said elongate alignment element includes a slot extending along said longitudinal axis and defining a pair of opposing side walls running from an upper portion of said elongate alignment element on said distal portion to an end of said elongate alignment element on said proximal portion;
    a bone anchor receptacle defined in said end of said elongate alignment element operable to receive at least a portion of a bone anchor;
    a locking pin assembly slidably positioned over a first portion of said upper portion of said elongate alignment element, said locking pin assembly comprising a plurality of locking pins extending longitudinally from and connected to an adjustment member, said adjustment member including a passage configured to slidably engage the first portion of said upper portion wherein said locking pin assembly is configured to place said bone anchor receptacle in either a locked or unlocked state, wherein in said locked state said bone anchor is fixedly secured in said bone anchor receptacle and in said unlocked state said bone anchor receptacle is capable of being disconnected from said bone anchor; and
    a locking cap slidably positioned over a second portion of said upper portion of said elongate alignment element,
    wherein at least one side wall of said pair of opposing side walls includes a cutout running from a position on said elongate alignment element through the end of said elongate alignment element thereby defining first and second lower portions outwardly flexible relative to one another such that the cutout expands as the first and second lower portions flex away from one another, and wherein at least a portion of said cutout defines a male member of said first lower portion and a female member of said second lower portion, the male member being receivable within said female member.

2. The alignment apparatus of claim 1, wherein said locking pin assembly includes at least one locking pin extending down said longitudinal axis of said elongate alignment element and configured to fit within a passage defined in said male member and said female member to resist relative movement between the first and second lower portions thereby placing said bone anchor in said locked state.

3. The alignment apparatus of claim 1, wherein said bone anchor receptacle includes at least one protrusion sized and configured to fit within a recess of said bone anchor.

4. The alignment assembly of claim 1, wherein said locking cap includes a retaining member having a passage oriented along a second longitudinal axis substantially parallel with said first longitudinal axis.

5. The alignment assembly of claim 1, wherein said locking cap includes a lever configured to controllably release said locking cap from said second portion of said upper portion of said elongate alignment element.

6. An alignment apparatus for use in correction of a deformity, comprising:
    an elongate alignment element extending along a first longitudinal axis and including a proximal portion and a distal portion, wherein said elongate alignment element includes a first slot extending along said longitudinal axis and defining a first pair of opposing side walls running from an upper portion of said elongate alignment element on said distal portion to an end of said elongate alignment element on said proximal portion;
    a bone anchor having a second pair of opposing side walls aligned with and connected to said first pair of said opposing side walls at said end of said elongate alignment element, wherein said first slot is aligned with a receiver of said bone anchor;
    a locking pin assembly slidably positioned over a first portion of said upper portion of said elongate alignment element, said locking pin assembly comprising a plurality of locking pins extending longitudinally from and connected to an adjustment member, said adjustment member including a passage configured to slidably engage the first portion of said upper portion; and
    a cap having a collet sized and configured to fit over an upper portion of said elongate alignment element, wherein said cap further includes a retaining member positioned along a side of said collet having an opening for receiving a rod,
    wherein at least one side wall of said pair of opposing side walls includes a cutout running from a position on said elongate alignment element through the end of said elongate alignment element thereby defining first and second lower portions outwardly flexible relative to one another such that the cutout expands as the first and second lower portions flex away from one another, and wherein at least a portion of said cutout defines a male member of said first lower portion and a female member of said second lower portion, the male member being receivable within said female member.

7. The alignment apparatus of claim 6, wherein said collet includes an alignment tab protruding inwardly from said collet, wherein said alignment tab is sized and configured to be positioned in a second slot on said upper portion thereby inhibiting rotational movement of said cap about said first longitudinal axis.

8. The alignment apparatus of claim 7, wherein said alignment tab is positioned on said collet such that said opening of said retaining member lies on a second longitudinal axis substantially parallel to said first longitudinal axis when said cap is positioned in said second slot.

9. The alignment apparatus of claim 8, wherein said opening of said retaining member on said cap and said first slot of said elongate alignment element are oriented in the same direction.

10. The alignment apparatus of claim 6, wherein said collet includes at least one protrusion sized and configured to fit in a groove on said upper portion thereby securing said cap to said elongate alignment element.

* * * * *